US009598359B2

(12) United States Patent
Allen et al.

(10) Patent No.: US 9,598,359 B2
(45) Date of Patent: *Mar. 21, 2017

(54) SULFONATES FROM NATURAL OIL METATHESIS

(75) Inventors: Dave R. Allen, Chicago, IL (US); Randal J. Bernhardt, Antioch, IL (US); Aaron Brown, Chicago, IL (US); Gary Luebke, Chicago, IL (US); Renee Luka, Park Ridge, IL (US); Andrew D. Malec, Chicago, IL (US); Ronald A. Masters, Glenview, IL (US); Patti Skelton, Winder, GA (US); Brian Sook, Lawrenceville, GA (US); Jeremy Aaron Weitgenant, Grayslake, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 17 days.

This patent is subject to a terminal disclaimer.

(21) Appl. No.: 13/880,007

(22) PCT Filed: Oct. 25, 2011

(86) PCT No.: PCT/US2011/057609
§ 371 (c)(1),
(2), (4) Date: May 15, 2013

(87) PCT Pub. No.: WO2012/061101
PCT Pub. Date: May 10, 2012

(65) Prior Publication Data
US 2013/0225473 A1  Aug. 29, 2013

Related U.S. Application Data

(60) Provisional application No. 61/406,570, filed on Oct. 25, 2010, provisional application No. 61/406,556, filed on Oct. 25, 2010, provisional application No. 61/406,547, filed on Oct. 25, 2010.

(51) Int. Cl.
*C07C 303/32* (2006.01)
*C07C 309/17* (2006.01)
*C11D 1/14* (2006.01)

(52) U.S. Cl.
CPC .......... *C07C 303/32* (2013.01); *C07C 309/17* (2013.01); *C11D 1/143* (2013.01)

(58) Field of Classification Search
None
See application file for complete search history.

(56) References Cited

U.S. PATENT DOCUMENTS

| 2,653,970 A | 9/1953 | Fessler et al. |
| 3,169,142 A | 2/1965 | Knaggs et al. |
| 3,231,606 A | 1/1966 | Fessler |
| 3,544,613 A | 12/1970 | Knaggs et al. |
| 3,645,716 A | 2/1972 | Rutkowski |
| 4,087,457 A | 5/1978 | Convers et al. |
| 4,148,821 A | 4/1979 | Nussbaum et al. |
| 4,275,013 A | 6/1981 | Tokosh et al. |
| 4,545,939 A | 10/1985 | Sekiguchi et al. |
| 4,545,941 A | 10/1985 | Rosenburg |
| 4,816,188 A | 3/1989 | Kitano et al. |
| 5,118,440 A | 6/1992 | Cutler et al. |
| 5,319,117 A | 6/1994 | Fabry et al. |
| 5,475,134 A | 12/1995 | Baker |
| 5,482,908 A | 1/1996 | Le-khac |
| 5,616,781 A | 4/1997 | Sajic et al. |
| 5,637,758 A | 6/1997 | Sajic et al. |
| 5,945,394 A | 8/1999 | Sajic et al. |
| 6,172,026 B1 | 1/2001 | Ospinal et al. |
| 7,576,227 B2 | 8/2009 | Bicerano et al. |
| 7,666,828 B2 * | 2/2010 | Bernhardt et al. ............ 510/495 |
| 7,820,612 B2 | 10/2010 | English, III |
| 7,879,790 B2 | 2/2011 | Bernhardt et al. |
| 7,884,064 B2 | 2/2011 | Bernhardt et al. |
| 7,960,599 B2 | 6/2011 | Millis et al. |
| 8,067,610 B2 | 11/2011 | Schrodi |
| 2008/0033026 A1 | 2/2008 | Zullo et al. |
| 2009/0264672 A1 | 10/2009 | Abraham et al. |
| 2010/0016198 A1 | 1/2010 | Bernhardt et al. |
| 2010/0017969 A1 | 1/2010 | Murphy et al. |
| 2010/0022429 A1 | 1/2010 | Bernhardt et al. |
| 2010/0145086 A1 | 6/2010 | Schrodi et al. |

(Continued)

FOREIGN PATENT DOCUMENTS

| GB | 1278421 | 6/1972 |
| WO | WO-2008048522 | 4/2008 |
| WO | 2009051300 | 4/2009 |

OTHER PUBLICATIONS

Tetrahedron 68 2012 , 1117.
Appl. Catal.A. 346 2009 , 158.
J.C. Mol., Topics in Catalysis 27 2004 , 97.
J. C. Mol., Green Chem., 4 2002 , 5.
Hasegawa et al., Org. Process Res. Dev. 7 (2003) 168.
Extended European Search Report mailed Aug. 7, 2015 in Application 11838505.3 (7 pages).

*Primary Examiner* — Necholus Ogden, Jr.
(74) *Attorney, Agent, or Firm* — Dilworth IP, LLC

(57) ABSTRACT

Sulfonate compositions are disclosed. The compositions include alkanesulfonates, alkenesulfonates, sultones, and hydroxy-substituted alkanesulfonates. The sulfonates comprise a reaction product of a metathesis-derived C10-C17 monounsaturated acid, octadecene-1,18-dioic acid, or their ester derivatives with a sulfonating or sulfitating agent. In one aspect, the sulfonate composition is a sulfo-estolide made by reacting a metathesis-derived C10-C17 monounsaturated acid or octadecene-1,18-dioic acid with a sulfonating agent, optionally in the presence of a saturated fatty acid. The sulfonates are valuable for a wide variety of end uses, including cleaners, fabric treatment, hair conditioning, personal care (liquid cleansing products, conditioning bars, oral care products), paint additives, antimicrobial compositions, agricultural uses, and oil field applications.

8 Claims, No Drawings

(56) References Cited

U.S. PATENT DOCUMENTS

| | | |
|---|---|---|
| 2010/0183539 A1 | 7/2010 | Bernhardt et al. |
| 2010/0184855 A1 | 7/2010 | Bernhardt et al. |
| 2010/0282467 A1 | 11/2010 | Hutchison et al. |
| 2011/0113679 A1 | 5/2011 | Cohen et al. |
| 2011/0313180 A1 | 12/2011 | Uptain et al. |
| 2012/0071676 A1 | 3/2012 | Schrodi et al. |
| 2012/0197031 A1 | 8/2012 | Firth et al. |
| 2013/0035502 A1 | 2/2013 | Cohen et al. |
| 2013/0035532 A1 | 2/2013 | Schrodi |

\* cited by examiner

SULFONATES FROM NATURAL OIL METATHESIS

FIELD OF THE INVENTION

The invention relates to sulfonates that originate from renewable resources, particularly natural oils and their metathesis products.

BACKGROUND OF THE INVENTION

Sulfonation is an important process for manufacturing anionic surfactants. Fatty acid derivatives, particularly fatty esters, are among many different starting materials that can be converted to valuable surfactants. For instance, a mixture of saturated and unsaturated fatty esters can be sulfonated with sulfur trioxide, then neutralized, to give an anionic surfactant useful in detergents (see, e.g., U.S. Pat. Nos. 4,545,939 and 4,816,188). Natural oils can be sulfonated (see, e.g., U.S. Pat. No. 5,319,117), but it is more common to use alkyl esters of fatty acids as starting materials. Saturated fatty methyl esters are frequently sulfonated to produce α-sulfonated methyl esters (see, e.g., U.S. Pat. Nos. 5,475,134; 5,945,394, and 5,616,781), which are used in laundry detergents (U.S. Pat. No. 7,820,612), soaps (U.S. Pat. No. 6,172,026), and light-duty liquid detergents (U.S. Pat. Nos. 5,118,440 and 5,637,758). Sulfo-estolides (see, e.g., U.S. Pat. Nos. 7,666,828 and 7,879,790 and U.S. Pat. Appl. Publ. No. 2010/0016198) are a particular class of sulfonated fatty esters that have value in laundry detergents, hard surface cleaners, and personal care applications.

The fatty acids or esters used to make these sulfonates and their derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, Green Chem. 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, fatty acid and ester sulfonates made from these feedstocks appear to be unknown. Moreover, sulfonates have not been made from the $C_{18}$ unsaturated diesters that can be made readily by self-metathesis of a natural oil.

In sum, traditional sources of fatty acids and esters used for making fatty ester sulfonates generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). New $C_{18}$ difunctional fatty ester sulfonates are also potentially available from oil or $C_{10}$ unsaturated acid or ester self-metathesis.

SUMMARY OF THE INVENTION

The invention relates to sulfonate compositions. The sulfonate compositions include alkanesulfonates, alkenesulfonates, sultones, and hydroxy-substituted alkanesulfonates. The sulfonates comprise a reaction product of a metathesis-derived $C_{10}$-$C_{17}$ monounsaturated acid, octadecene-1,18-dioic acid, or their ester derivatives with a sulfonating or sulfitating agent. In one aspect of the invention, the sulfonate composition is a sulfo-estolide made by reacting a metathesis-derived $C_{10}$-$C_{17}$ monounsaturated acid or octadecene-1,18-dioic acid with a sulfonating agent. The sulfonates are valuable for a wide variety of end uses, including cleaners, fabric treatment, hair conditioning, personal care (liquid cleansing products, conditioning bars, oral care products), paint additives, antimicrobial compositions, agricultural uses, and oil field applications.

DETAILED DESCRIPTION OF THE INVENTION

In one aspect, the invention relates to sulfonate compositions that comprise reaction products of a metathesis-derived $C_{10}$-$C_{17}$ monounsaturated acid, octadecene-1,18-dioic acid, or their ester derivatives with a sulfonating or sulfitating agent.

The $C_{10}$-$C_{17}$ monounsaturated acid, octadecene-1,18-dioic acid, or their ester derivatives used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived sulfonates and derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to sulfonate compositions made from them, including, for example, modified physical form, melting range, compactability, and other important properties. These differences should allow formulators that use sulfonates greater latitude or expanded choice as they use them in cleaners, fabric treatment, personal care, agricultural uses, and other end uses.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making the inventive sulfonate compositions.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive sulfonate compositions.

An alternative to using a natural oil as a feedstock to generate the $C_{10}$-$C_{17}$ monounsaturated acid, octadecene-1,18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

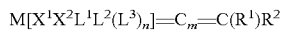

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

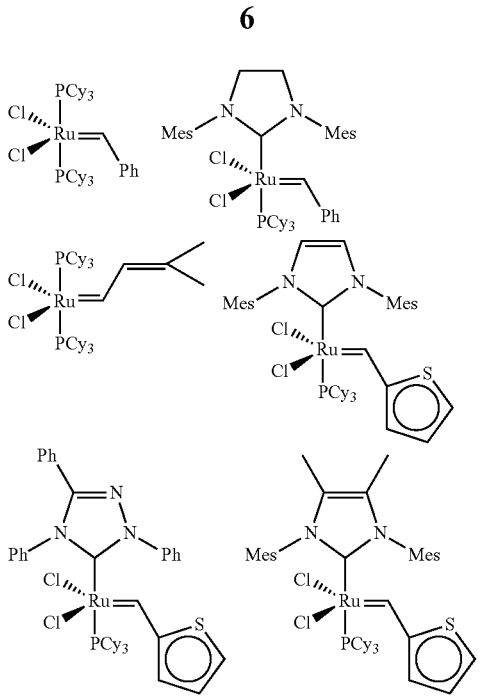

Heterogeneous catalysts suitable for use in the self- or cross-metathesis reaction include certain rhenium and molybdenum compounds as described, e.g., by J. C. Mol in Green Chem. 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

The sulfonates are made by reacting a metathesis-derived $C_{10}$-$C_{17}$ monounsaturated acid, octadecene-1,18-dioic acid, or their ester derivatives with a sulfonating or sulfitating agent.

In one aspect, the ester derivative is a lower alkyl ester, especially a methyl ester. The lower alkyl esters are preferably generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be used "as is" to make the inventive sulfonates or they can be purified to isolate particular alkyl esters prior to making sulfonates.

The skilled person will appreciate that "ester derivative" here encompasses other acyl equivalents, such as acid chlorides, acid anhydrides, or the like, in addition to the lower alkyl esters and glyceryl esters discussed above.

Sulfonation is performed using well-known methods, including reacting the olefin with sulfur trioxide. Sulfonation may optionally be conducted using an inert solvent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Sulfitation is accomplished by combining an olefin in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

Sulfonation or sulfitation of the metathesis-derived $C_{10}$-$C_{17}$ monounsaturated acid, octadecene-1,18-dioic acid, or their ester derivatives provides reaction products that include one or more of alkanesulfonates, alkenesulfonates, sultones, hydroxy-substituted alkanesulfonates. Mixtures of these reaction products are typical (see, e.g., sulfonates 010-1 and 012-1, in the examples below).

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

Some preferred alkanesulfonates have the structure:

wherein X is H, an alkali metal, ammonium, or alkylammonium cation; R is X or $C_1$-$C_{10}$ alkyl or aryl; n=9-16; and the S atom is bonded to any carbon on the $C_nH_{2n}$ chain. Preferably, the S atom is bonded at the C9 or C10 position relative to the carbonyl carbon. Preferably, the $C_nH_{2n}$ chain is linear. When n=9, the S atom is bonded to C10.

Additional preferred alkanesulfonates have the structure:

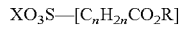

wherein X is H, an alkali metal, ammonium, or alkylammonium cation; R is X or $C_1$-$C_{10}$ alkyl or aryl; n=9-16; and the S atoms are bonded to any pair of adjacent carbons on the $C_nH_{2n-1}$ chain. Preferably, the S atoms are bonded at the C9 and C10 positions relative to the carbonyl carbon. Preferably, the $C_nH_{2n-1}$ chain is linear. When n=9, an S atom is bonded to C10.

Some preferred alkenesulfonates have the structure:

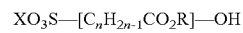

wherein X is H, an alkali metal, ammonium, or alkylammonium cation; R is X or $C_1$-$C_{10}$ alkyl or aryl; n=9-16; and the S atom is bonded to any carbon on the $C_nH_{2n-2}$ chain. Preferably, the S atom is bonded at the C9 or C10 position relative to the carbonyl carbon. In more preferred alkenesulfonates, the S atom is bonded at the C9 or C10 position and the unsaturation is allylic with respect to sulfur. Preferably, the $C_nH_{2n-2}$ chain is linear. When n=9, the S atom is bonded to C10.

Some preferred hydroxyalkanesulfonates have the structure:

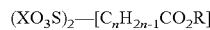

wherein X is H, an alkali metal, ammonium, or alkylammonium cation; R is X or $C_1$-$C_{10}$ alkyl or aryl; n=9-16; the S atom is bonded to any carbon on the $C_nH_{2n-1}$ chain, and the OH group is bonded to a carbon that is α, β, or γ relative to the carbon that is substituted with the —$SO_3X$ group. Preferably, the S atom is bonded at the C9 or C10 position relative to the carbonyl carbon. Preferably, the $C_nH_{2n-1}$ chain is linear. When n=9, the S atom is bonded to C10.

Preferred sultones are β-, γ-, or δ-sultones, which have four, five, or six-membered rings, respectively, that incorporate a —$SO_2$—O— group within the ring. As the skilled person appreciates, the sultones are typically intermediates that, through appropriate processing conditions such as treatment with aqueous alkali, may be converted to hydroxyalkanesulfonates and/or alkenesulfonates.

Some specific examples of $C_{10}$, $C_{12}$ and $C_{16}$-based sulfonate mixtures appear below:

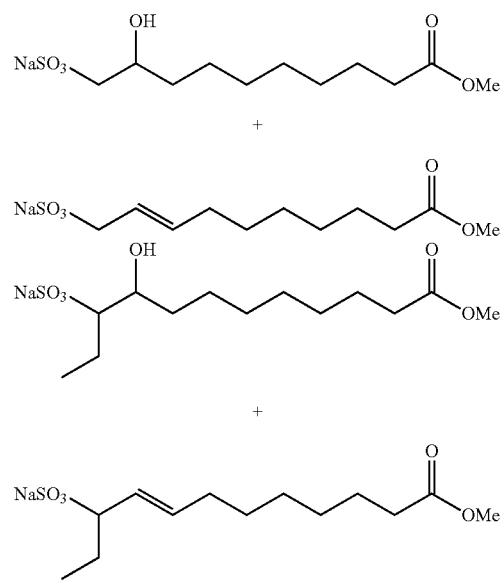

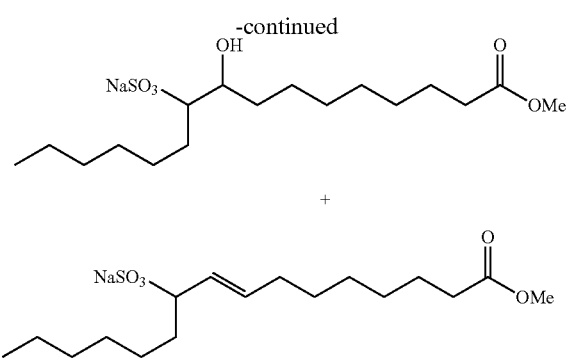

ably a saturated $C_6$ to $C_{18}$ carboxylic acid. Suitable sulfo-estolides have the structural moiety:

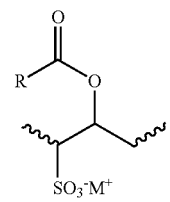

Some specific examples of $C_{18}$-based sulfonate mixtures:

in which R is a linear or branched, saturated or unsaturated, substituted or unsubstituted alkyl radical and M is hydrogen

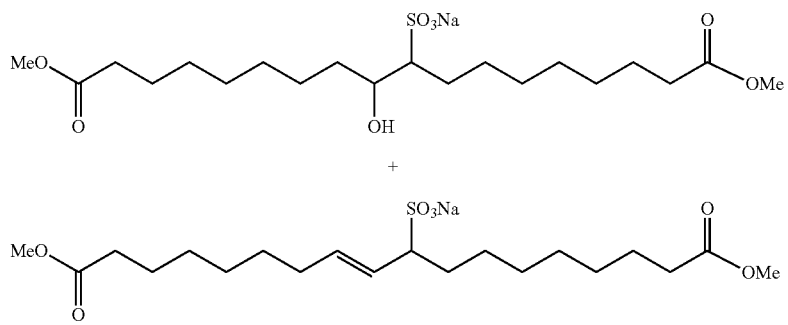

In one aspect of the invention, the sulfonate composition is a sulfo-estolide made by reacting a metathesis-derived $C_{10}$-$C_{17}$ monounsaturated acid or octadecene-1,18-dioic acid with a sulfonating agent. Optionally, the sulfo-estolide is made by reacting the metathesis-derived $C_{10}$-$C_{17}$ monounsaturated acid, octadecene-1,18-dioic acid, or their ester derivatives with a sulfonating agent in the presence of an additional carboxylic acid. The additional carboxylic acid can be saturated or unsaturated and branched or unbranched. In some instances, the additional carboxylic acid is preferor a mono or divalent cation (shown as monovalent above) such as sodium, potassium, calcium, trialkanolammonium, or the like.

Sulfonation converts some of the carbon-carbon double bonds in the metathesis-derived acid or ester reactant to sultones, particularly β-sultones. These are believed to undergo nucleophilic attack by a carboxylic oxygen to give a sulfo-estolide. The scheme below depicts a possible reaction pathway using a $C_{10}$ unsaturated fatty acid as the reactant:

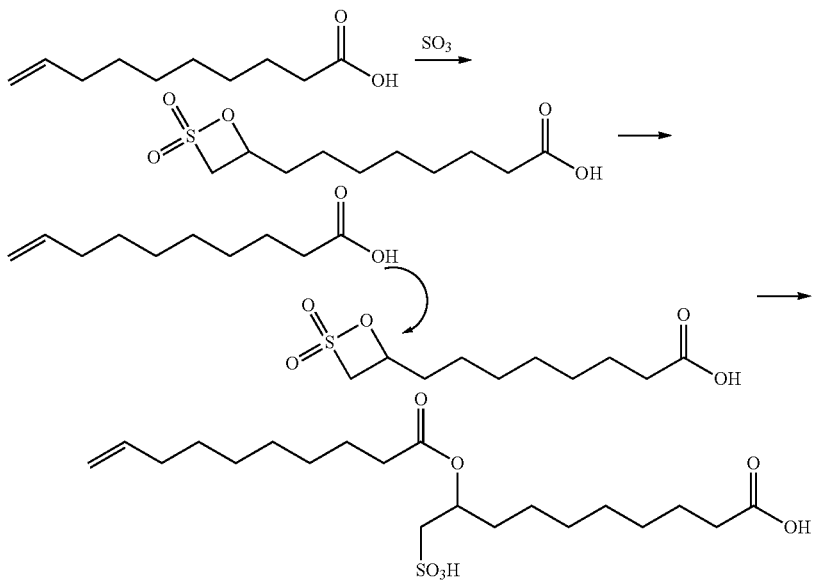

As the skilled person will appreciate, the product mixture will be more complex than shown above, for example, when the starting material is a mixture of different unsaturated acids and/or esters, or when the sulfonation is performed under conditions that promote isomerization of the carbon-carbon double bond.

The product mixture may comprise oligomers, for example dimers and trimers that are formed by the ring-opening of β-sultone with carboxlic acids of sulfo-estolides. The degree of oligomerization is optionally controlled by adjusting the proportion of saturated and unsaturated fatty acid components, as the saturated fatty acid serves as a chain terminator. For examples of reactions used to produce sulfo-estolides, see U.S. Pat. Nos. 7,879,790 and 7,666,828 and U.S. Pat. Appl. Publ. No. 2010/0016198, the teachings of which are incorporated herein by reference.

Some sulfo-estolides have the structure:

$$XO_3S-[C_nH_{2n-1}CO_2R]-OCOR^1$$

wherein X is H, an alkali metal, ammonium, or alkylammonium cation; R is X or $C_1$-$C_{10}$ alkyl or aryl; n=9-16; $R^1$ is a $C_8$ to $C_{18}$ saturated or monounsaturated group. The S atom and the —$OCOR^1$ group are bonded to vicinal carbons on the $C_nH_{2n-1}$ chain. When n=9, the S atom is preferably bonded at the C10 position relative to the carbonyl carbon. Some specific examples of sulfo-estolides:

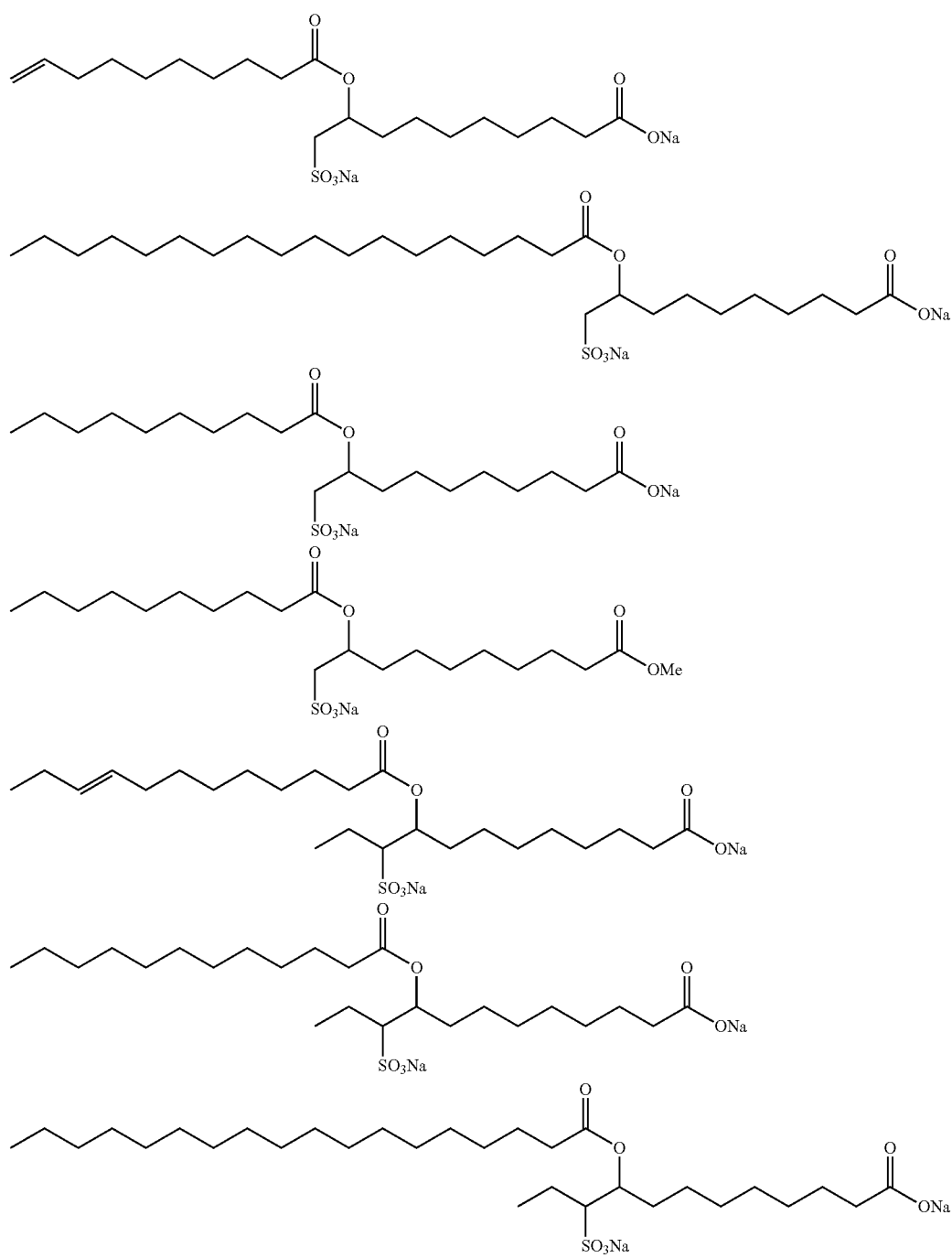

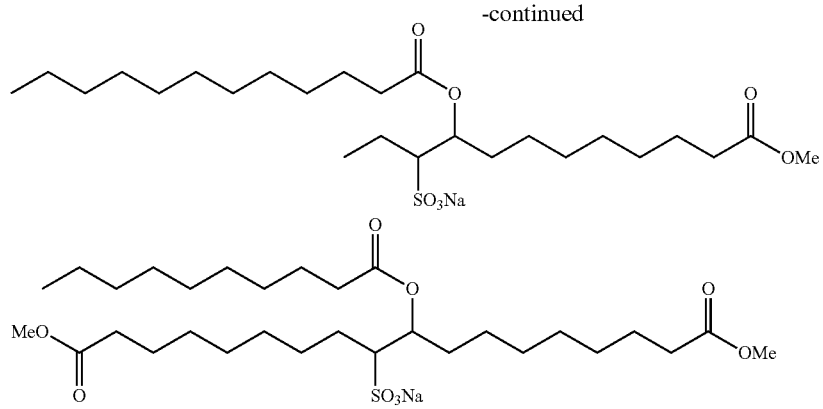

The sulfonates can be incorporated into many compositions for use as, for example, surfactants, emulsifiers, skin-feel agents, film formers, rheological modifiers, biocides, biocide potentiators, solvents, release agents, and conditioners. The compositions find value in diverse end uses, such as personal care (liquid cleansing products, conditioning bars, oral care products), household products (liquid and powdered laundry detergents, liquid and sheet fabric softeners, hard and soft surface cleaners, sanitizers and disinfectants), and industrial or institutional cleaners.

The sulfonates can be used in emulsion polymerizations, including processes for the manufacture of latex. They can be used as surfactants, wetting agents, dispersants, or solvents in agricultural applications, as inert ingredients in pesticides, or as adjuvants for delivery of pesticides for crop protection, home and garden, and professional applications. The sulfonates can also be used in oil field applications, including oil and gas transport, production, stimulation and drilling chemicals, reservoir conformance and enhancement uses, and specialty foamers. The compositions are also valuable as foam moderators or dispersants for the manufacture of gypsum, cement wall board, concrete additives and firefighting foams. The compositions are used as coalescents for paints and coatings, and as polyurethane-based adhesives.

In food and beverage processing, the sulfonates can be used to lubricate the conveyor systems used to fill containers. When combined with hydrogen peroxide, the sulfonates can function as low foaming disinfectants and sanitization agents, odor reducers, and as antimicrobial agents for cleaning and protecting food or beverage processing equipment. In industrial, institutional and laundry applications, the sulfonates, or their combination with hydrogen peroxide, can be used to remove soil and sanitize and disinfect fabrics and as antimicrobial film-forming compositions on hard surfaces.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

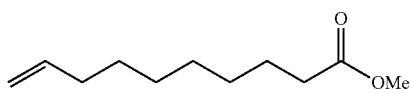

-continued

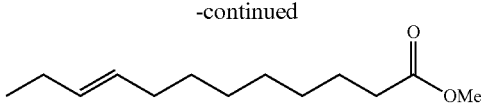

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt/%), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 ptorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 ptorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (μtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Preparation of Methyl 9-Hexadecenoate ("C16-0") feedstock

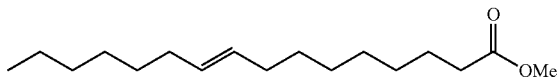 [SMILES: CCCCCC/C=C/CCCCCCCC(=O)OC]

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

C10-1: C10 Sulfonate

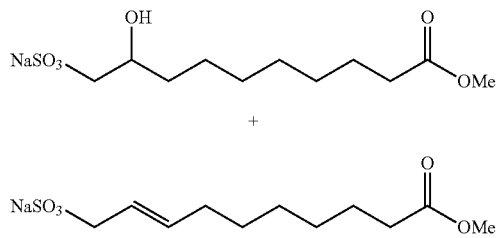

In a batch reactor maintained at 20° C. under a nitrogen flow (2 L/min.), methyl decenoate (106.7 g, 0.58 mol) is added to methylene chloride (100 mL). Sulfur trioxide (46.1 g, 0.58 mol) is evaporated over 30 min. via a 140° C. flash-pot and is bubbled through the reactor using the nitrogen stream. The addition rate of $SO_3$ is adjusted to keep the reaction temperature at or below 35° C. At the end of the addition, the reaction mixture is maintained for an additional 5 min. and the mixture is then concentrated under vacuum. The acid product is then digested for 1 h at 50° C. Methanol (7.5 g) is added to the acid (~150 g), and the solution is heated to 65° C. for 1 h. The mixture is cooled to 0° C., and a solution prepared from 50% aqueous NaOH (16.48 g) and water (142.6 g) is slowly added. When the addition is complete, the pH is about 1.5. Additional 50% aq. NaOH solution (4.2 g) is added to adjust the pH to about 7. The mixture is heated to 85° C. while monitoring pH. The pH is kept between 5 and 7 by adding more 50% aq. NaOH. The stirred solution is heated at 85° C. for a total of 8 h under a nitrogen purge to remove methanol and completely hydrolyze sultones. The resulting product ("C10-1") is a mixture that includes an alkenesulfonate and a hydroxyalkane sulfonate. Moisture: 46.7 wt. %; sodium sulfate: 0.27 wt. %.

C10-36: C10 Fatty Acid

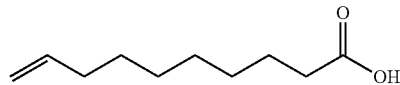

Methyl ester C10-0 (390.2 g) is charged to a round-bottom flask equipped with an overhead stirrer. After warming to 70° C., a mixture of KOH in glycerol (16% KOH, 523 g) is added. The mixture is warmed to 100° C. and more solid KOH (35.1 g) is added. The mixture stirs for ~17 h. Gas chromatography shows ~94% conversion to the free fatty acid. More solid KOH (10 g) is added, and the mixture stirs at 100° C. for 4 h. Conversion by GC is now >97%. The mixture stirs at 100° C. for another 4 h and then cools to 80° C. Water (400 mL) and 30% aq. $H_2SO_4$ (500 mL) are added. The mixture stirs at 80° C. for ~1 h. The layers are separated, and the aqueous layer is removed. More water (500 mL) is added, and the mixture is again heated to 80° C. with stirring for 30 min. The layers are again separated, and the aqueous phase is discarded. The washing process (with 500 mL of water) is repeated two more times. The resulting free fatty acid, C10-36, is stripped under vacuum (80° C., 2 h) and is thereafter used without further purification. Yield: 357 g. $^1$H NMR results are consistent with the proposed structure. Moisture: 315 ppm.

C12-1: C12 Sulfonate

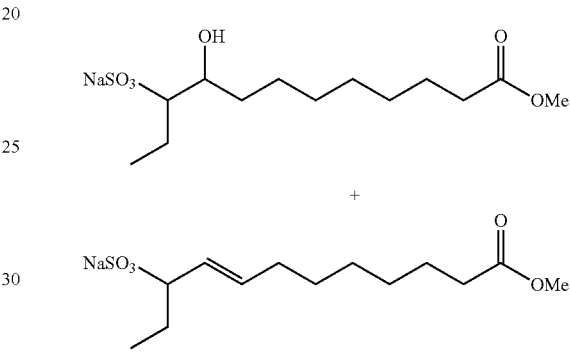

C12-1 is synthesized in a manner similar to C10-1 using C12-0 (106.7 g, 0.579 mol), methylene chloride (100 mL), and sulfur trioxide (46.1 g, 0.575 mol). Digestion is carried out for 1 h at 65° C. Methanol (7.7 g) is added, and the mixture is warmed to 65° C. for 1 h. The acid is neutralized at 0° C. using aqueous sodium hydroxide (20.3 g of 50% aq. NaOH in 141.6 g of water). Hydrolysis is carried out at 85° C. until determined complete by $^1$H NMR. The pH is maintained between 5-7 with further additions of 50% NaOH (aq). After the hydrolysis, a material found to be the starting methyl ester oils out of solution and forms a small layer on top of the neutralized material. The oil layer is removed and the aqueous layer is analyzed. $^1$H NMR data supports the proposed composition. Moisture: 47.1 wt. %; pH: 8.58 (1% in 9:1 IPA/water); sodium sulfate: 0.52 wt. %; unsulfonated matter: 2.05 wt. %; methanol: 0.53 wt. %.

C12-39: C12 Fatty Acid

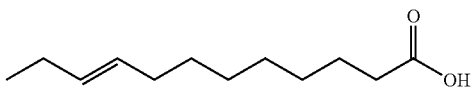

A round-bottom flask equipped with an overhead stirrer, thermocouple, and nitrogen inlet is charged with KOH pellets (158 g) and glycerol (832 g). The mixture is stirred and warmed to 100° C. After 1 h, the homogeneous solution is allowed to cool to 75° C. Methyl ester C12-0 (500 g, 2.35 mol) is added. The mixture is heated to 120° C. and is held for 4 h. GC analysis indicates complete conversion to the fatty acid. After cooling to 85° C., 30% aq. sulfuric acid (1109 mL) is added in one portion. The resulting two-phase mixture is stirred at 85° C. for 30 min. The two phases quickly separate, and the aqueous phase is removed. The oil phase is washed with water (3×1000 mL) followed by drying under vacuum (100° C., 2 h). Fatty acid C12-39 is used without further purification. Yield: 452 g. $^1$H NMR results support the proposed structure.

C16-1: C16 Sulfonate

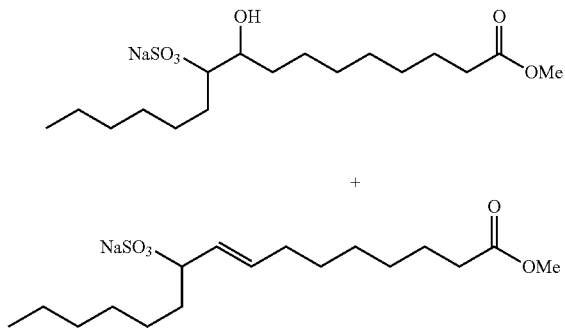

C16-1 is synthesized in a manner similar to C10-1 using C16-0 (110.2 g, 0.410 mol), methylene chloride (100 mL), and sulfur trioxide (34.4 g, 0.430 mol). Digestion is carried out for 1 h at 65° C. Methanol (7 g) is added, and the mixture is warmed to 65° C. for 1 h. The acid is neutralized at 0° C. using aqueous sodium hydroxide (20.9 g of 50% aq. NaOH in 118.3 g of water). Hydrolysis is carried out at 95° C. until determined complete by $^1$H NMR. The pH is maintained between 5-7 with further additions of 50% aq. NaOH. The desired solids level is maintained with water additions during hydrolysis. $^1$H NMR data supports the proposed composition. Moisture: 47.1 wt. %; pH: 4.6 (1% in 9:1 IPA/water); sodium sulfate: 1.8 wt. %; unsulfonated matter: 10.47 wt. %.

C10-32: C10 UFA SLA

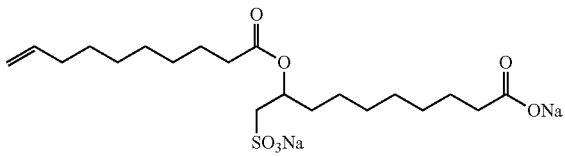

The procedure used to prepare C10-1 is generally followed with methylene chloride (100 mL) and sulfur trioxide (51.6 g, 0.644 mol), except that fatty acid C10-36 (109.6 g, 0.644 mol) is used instead of methyl ester C10-0. During SO$_3$ addition, more methylene chloride (100 mL) is added to reduce viscosity. The acid is neutralized with water (151.0 g) followed by 50% aq. NaOH (41.69 g). Hydrolysis is carried out at 85° C. and pH is maintained with additional 50% NaOH (aq) additions. $^1$H NMR of the sulfo-estolide product, C10-32, supports the proposed structure. Analysis shows: pH: 5.25 (as is); moisture: 51.6 wt. %; sodium sulfate: 0.51 wt. %; unsulfonated matter: 0.79 wt. %.

C10-33: C10 UFA C18 FA (80:20) SLA

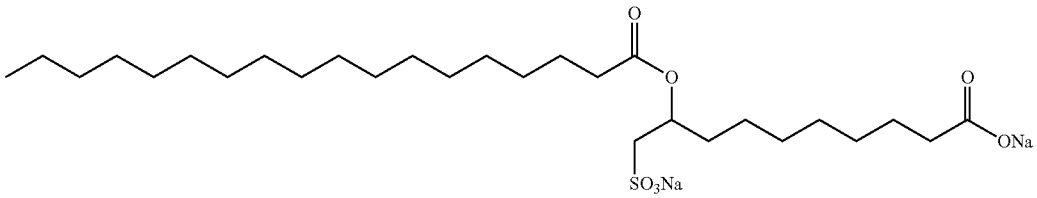

The procedure used to prepare C10-1 is generally followed with methylene chloride (200 mL) and sulfur trioxide (45.5 g, 0.569 mol), except that an 80:20 (w/w) blend of C10-36 and stearic acid (115.3 g, 0.542 mol of unsaturation) is used instead of methyl ester C10-0. During SO$_3$ addition, more methylene chloride (100 mL) is added and the reaction temperature is raised from 15° C. to 20° C. The mixture is then digested for 1.5 h at 50° C. The acid product is neutralized using water (161.5 g) and 50% aq. NaOH (42.9 g). Hydrolysis is carried out at 85° C. Throughout the hydrolysis, a two-phase mixture is present. The mixture cools to room temperature and each phase is analyzed by $^1$H NMR. The product is allowed to concentrate in the open air for 2 days. The resulting paste is warmed to 75° C., homogenized by stirring, and cooled to room temperature. Analysis of the sulfo-estolide shows: pH: 7.89 (1% in 9:1 IPA/water); moisture: 23.7 wt. %; inorganic sulfate: 0.94 wt. %; unsulfonated matter: 10.5 wt. %. $^1$H NMR analysis supports the proposed composition.

C10-34: C10 UFA C10 FA (80:20) SLA

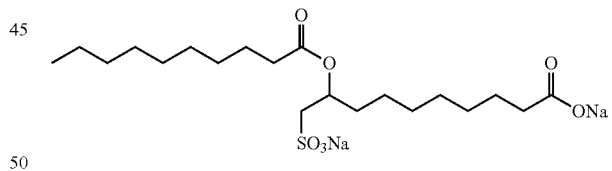

The procedure used to prepare 010-1 is generally followed with methylene chloride (100 mL) and sulfur trioxide (45.2 g, 0.565 mol), except that an 80:20 (w/w) blend of 010-36 and decanoic acid (115.7 g, 0.545 mol of unsaturation) is used instead of methyl ester C10-0. During SO$_3$ addition, more methylene chloride (100 mL) is added. The mixture is digested for 1 h at 50° C. The acid product is diluted with water (175.2 g) and then 50% aq. NaOH (42.9 g). Hydrolysis is carried out at 85° C. and pH is maintained between 5-7 using 50% NaOH (aq). $^1$H NMR analysis of sulfo-estolide 010-34 supports the proposed composition. Analysis shows: pH: 5.2 (1% in 9:1 IPA/water); sodium sulfate: 0.74 wt. %; unsulfonated matter: 5.96 wt. %; moisture: 58.1 wt. %.

C10-35: C10 UME C10 FA (60:40) SLA

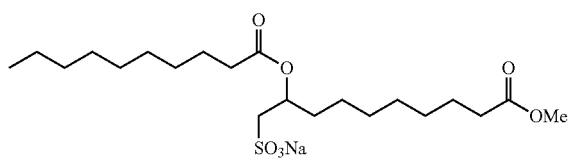

The procedure used to prepare O10-1 is generally followed with methylene chloride (100 mL) and sulfur trioxide (37.5 g, 0.469 mol), except that a 60:40 (w/w) blend of methyl ester O10-0 and decanoic acid (134.3 g, 0.447 mol of unsaturation) is used instead of O10-0 only. The mixture is digested for 1 h at 50° C. The acid is neutralized using water (106.1 g) followed by 50% aq. NaOH (28.8 g). Hydrolysis is carried out at 85° C. and pH is maintained between 5-7 using 50% NaOH (aq). $^1$H NMR results support the proposed structure for sulfo-estolide O10-35. Analysis shows: pH: 7.22 (1% in 9:1 IPA/water); moisture: 41.1 wt. %; sodium sulfate: 0.15 wt. %; unsulfonated matter: 11.8 wt. %; methanol: 0.48 wt. %.

C12-34: C12 UFA SLA

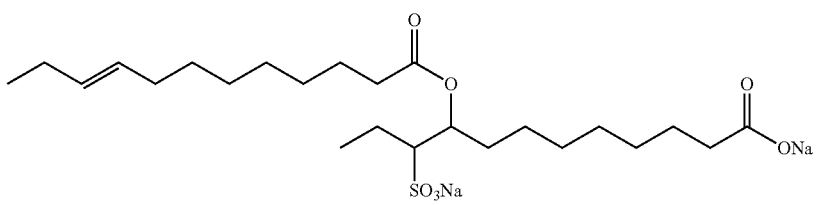

The procedure used to prepare C10-1 is generally followed with methylene chloride (100 mL) and sulfur trioxide (51.1 g, 0.635 mol), except that fatty acid C12-39 (120.5 g, 0.608 mol) is used instead of methyl ester C10-0. The mixture is digested for 70 min. at 50° C. The acid product is neutralized with water (154.3 g) followed by 50% aq. NaOH (47.1 g). Hydrolysis is carried out at 85° C. and pH is maintained between 5-7 using 50% NaOH (aq). $^1$H NMR results support the proposed composition for sulfo-estolide C12-34. Analysis shows: pH: 7.7 (1% in 9:1 IPA/water); moisture: 49.5 wt. %; sodium sulfate: 0.69 wt. %; unsulfonated matter: 0.71 wt. %.

C12-35: C12 UFA C12 FA (80:20) SLA

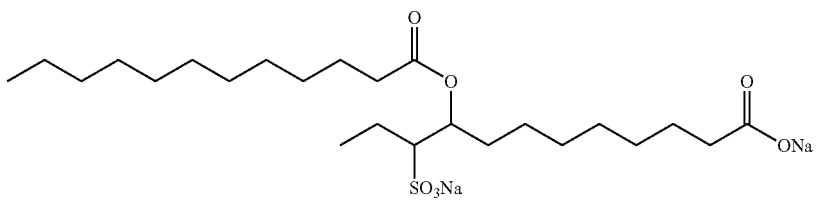

The procedure used to prepare C10-1 is generally followed with methylene chloride (100 mL) and sulfur trioxide (40.2 g, 0.502 mol), except that an 80:20 (w/w) blend of C12-39 and lauric acid (110 g, 0.445 mol of unsaturation) is used instead of methyl ester C10-0. The mixture is digested for 1 h at 50° C. The acid product is neutralized with water (106.2 g) and aq. 50% NaOH (45.2 g). Hydrolysis is carried out at 85° C. and pH is maintained between 5-7 using 50% NaOH (aq). $^1$H NMR results support the proposed composition for sulfo-estolide C12-35. Analysis shows: pH: 8.22 (1% in 9:1 IPA/water); moisture: 39.5 wt. %; sodium sulfate: 0.8 wt. %; unsulfonated matter: 6.44 wt. %.

C12-36: C12 UFA C18 FA (80:20) SLA

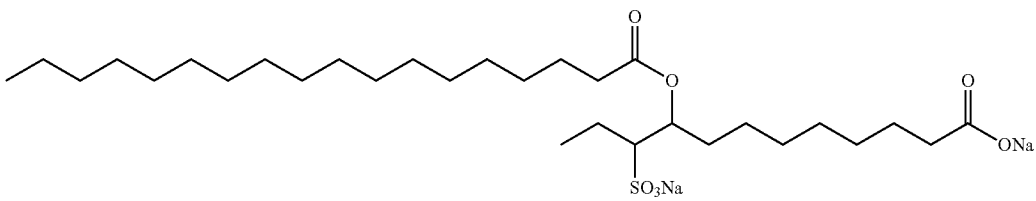

The procedure used to prepare C10-1 is generally followed with methylene chloride (200 mL) and sulfur trioxide (39.5 g, 0.494 mol), except that an 80:20 (w/w) blend of C12-39 and stearic acid (116.8 g, 0.471 mol of unsaturation) is used instead of methyl ester C10-0. During the $SO_3$ addition, more methylene chloride (100 mL) is added. The mixture is digested for 1 h at 65° C. The acid product is neutralized using water (108.8 g) and 50% aq. NaOH (48.3 g). Hydrolysis is carried out at 85° C. and pH is maintained between 5-7 using 50% NaOH (aq). $^1$H NMR results support the proposed composition for sulfo-estolide C12-36. Analysis shows: pH: 7.92 (1% in 9:1 IPA/water); moisture: 31.0 wt. %; sodium sulfate: 0.95 wt. %; unsulfonated matter: 5.32 wt. %.

C12-37: C12 UME C12 FA (60:40) SLA

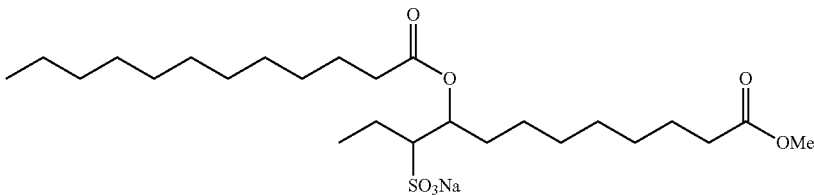

The procedure used to prepare C10-1 is generally followed with methylene chloride (100 mL) and sulfur trioxide (33.7 g, 0.421 mol), except that a 60:40 (w/w) blend of methyl ester C12-0 and lauric acid (142.7 g, 0402 mol of unsaturation) is used instead of C10-0 only. The mixture is digested for 1 h at 65° C. The acid product is neutralized with water (116.4 g) and 50% aq. NaOH (35.7 g). Hydrolysis is carried out at 85° C. and pH is maintained between 5-7 using 50% NaOH (aq). $^1$H NMR results support the proposed composition for sulfo-estolide C12-37. Analysis shows: pH: 7.63 (1% in 9:1 IPA/water): methanol: 0.2 wt. %; 2-propanol: 0.44 wt. %; moisture=43.3 wt. %; sodium sulfate: 0.84 wt. %; unsulfonated matter: 12.9 wt. %.

C12-43: C12 UFA C12 FA (80:20) SLA, Ca Salt

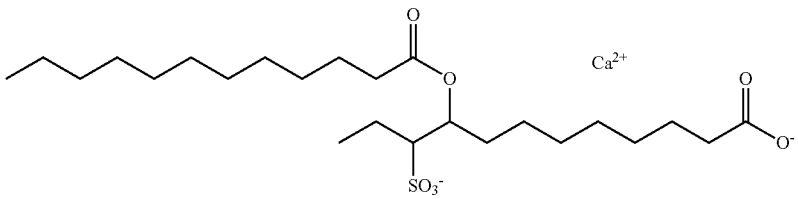

The procedure used to prepare C10-1 is generally followed with methylene chloride (100 mL) and sulfur trioxide (75.7 g, 0.946 mol), except that a 80:20 (w/w) blend of fatty acid C12-39 and lauric acid (224.1 g, 0.897 mol of unsaturation) is used instead of C10-0 only. The mixture is digested for 1 h at 60° C. The acid product (151.9 g.) is neutralized with Ca(OH)$_2$ in a water/methanol solution. Hydrolysis is carried out at 85° C. and pH is maintained between 5-7 with Ca(OH)$_2$. After hydrolysis, two layers form and the top layer is removed. The lower layer is found to contain the desired material and this mixture is heated to 80° C. for 2 h under vacuum to remove water/methanol. $^1$H NMR results support the proposed composition for sulfo-estolide C12-43. Analysis shows: pH: 5.7 (10% in water); solids: 90.6 wt. %.

C12-44: C12 UFA C12 FA (80:20) SLA, TEA Salt

Eight samples of methyl 9-dodecenoate (10.6 g each, see Table 2) are warmed to 50° C. and degassed with argon for 30 min. A metathesis catalyst ([1,3-bis-(2,4,6-trimethylphenyl)-2-imidazolidinylidene]dichlororuthenium(3-methyl-2-butenylidene)-(tricyclohexylphosphine), product of Materia) is added to the methyl 9-dodecenoate (amount indicated in Table 2) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 2. "Mix-0" is an 80:20 trans-/cis-isomer mixture obtained from the reaction mixture. Crystallization provides the all-trans-isomer feed, "C18-0."

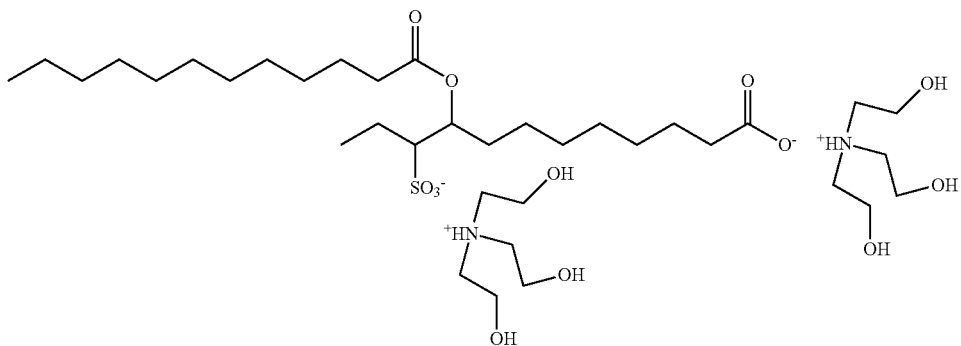

The acid product made in the procedure for C12-43 (151.9 g) is neutralized with triethanolamine (76.4 g) and the material is warmed to 85° C. until $^1$H NMR indicates complete disappearance of sultones. $^1$H NMR results support the proposed composition for sulfo-estolide C12-44. Analysis shows: pH: 6.57 (1% in 9:1 IPA/water); solids: 99.4 wt. %.

Feedstock Synthesis

Preparation of Dimethyl 9-Octadecene-1,18-dioate ("Mix-0" or "C18-0")

TABLE 2

Self-Metathesis of Methyl 9-Dodecanoate

| Sample | Catalyst Loading (ppm mol/mol)* | Reaction Time (hr) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

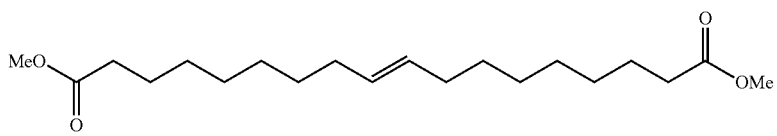 [SMILES: COC(=O)CCCCCCC/C=C/CCCCCCCC(=O)OC]

C18-1: C18 Sulfonate

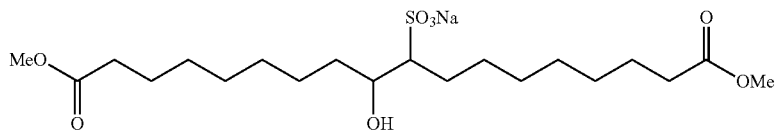

+

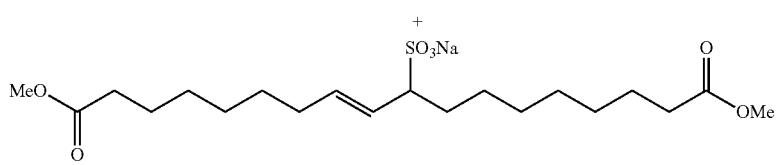

The procedure used to synthesize C10-1 is generally followed using C18-0 (125.8 g, 0.370 mol), methylene chloride (100 mL), and sulfur trioxide (30.4 g, 0.380 mol). Digestion is carried out for 1 h at 65° C. Methanol (7.24 g) is added, and the mixture is warmed to 65° C. for 1 h. The acid is neutralized at 0° C. using aqueous sodium hydroxide (a mixture of 19.2 g of 50% NaOH and 107 g of water). Hydrolysis is carried out at 85° C. until $^1$H NMR shows complete conversion. The pH is maintained between 5-7 with further additions of 50% NaOH (aq). After the hydrolysis, a small layer of oil, found to be starting methyl ester, forms on the surface and is removed. $^1$H NMR results supported the proposed composition for C18-1. Analysis shows: pH: 5.56 (1% in 9:1 IPA/water); moisture: 30.7 wt. %; sodium sulfate: 1.59 wt. %; unsulfonated matter: 5.62 wt. %.

C18-63: DBE C10 FA (60:40) SLA

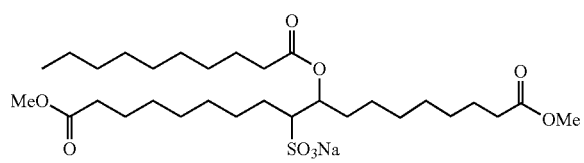

The procedure used to prepare C10-1 is generally followed with methylene chloride (100 mL) and sulfur trioxide (20.5 g, 0.256 mol), except that a 60:40 (w/w) blend of dibasic methyl ester C18-0 and decanoic acid (134.8 g, 0.245 mol of unsaturation) is used instead of C10-0 only. The mixture is digested for 165 min at 65° C. The acid product is neutralized using water (166.1 g) and aq. 50% NaOH (32.0 g). Hydrolysis is carried out at 85° C. and pH is maintained between 5-7 using 50% NaOH (aq). $^1$H NMR results support the proposed sulfo-estolide composition, C18-63. Analysis shows: pH: 7.02 (as is); methanol: 0.16 wt. %; 2-propanol: 0.09 wt. %; sodium sulfate: 0.67 wt. %; unsulfonated matter: 10.4 wt. %; moisture: 51.5 wt. %.

C18-64: DBE C10 FA (75:25) SLA

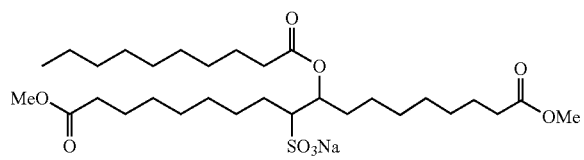

The procedure used to prepare C10-1 is generally followed with methylene chloride (100 mL) and sulfur trioxide (19.8 g, 0.247 mol), except that a 75:25 (w/w) blend of dibasic methyl ester C18-0 and decanoic acid (103.9 g, 0.236 mol of unsaturation) is used instead of C10-0 only. The mixture is placed in a 65° C. oven for 2 h, then a 72° C. oven for another 1 h. The acid product is neutralized using water (170 g) and aq. 50% NaOH (19.8 g). Hydrolysis is carried out at 85° C. and pH is maintained between 5-7 using 50% NaOH (aq). $^1$H NMR results support the proposed composition for sulfo-estolide C18-64. Analysis shows: pH: 8.09 (1% in 9:1 IPA/water); methanol: 0.12 wt. %; sodium sulfate: 0.98 wt. %; unsulfonated matter: 7.8 wt. %; moisture: 52.2 wt. %.

Agricultural Products: Anionic Emulsifiers

Anionic surfactant samples contain a relatively high amount of water (>20%) and are prepared as oil-in-water (EW) concentrates. These are tested against controls containing a standard surfactant or a blank. Enough is formulated to test two water hardnesses (34 ppm and 1000 ppm) for each of the three samples.

Sample Preparation:

Pyraflufen (97.8% active, 0.30 g) is combined and with Stepan® C-25 (methyl caprylate/caprate, 7.20 g), and N-methyl-2-pyrrolidone (1.20 g), and the mixture is stirred magnetically until dissolved. In a separate container, Toximul® 8242 (castor oil ethoxylate, POE 40, product of Stepan) 0.96 g), Ninex® MT-630F (fatty acid ethoxylate, POE 30, Stepan, 0.19 g), Ninex® MT-615 (fatty acid ethoxylate, POE 15, Stepan, 0.17 g), Aromatic 150 solvent (ExxonMobil, 0.37 g), and the anionic sample to be tested (0.71 g) are blended. If needed, the anionic sample is melted in an oven at 50-60° C. prior to combining with the other surfactants. When the pyraflufen has dissolved, the entire surfactant blend is added and magnetically stirred until homogeneous. Deionized water (0.90 g) is slowly added with mixing to prevent gelling. Turbidity changes are noted and recorded.

Control 1 Sample:

The same procedure is followed except that the anionic sample is replaced with Ninate® 60L (calcium alkylbenzenesulfonate, Stepan, 0.71 g).

Control 2 Sample:

No Ninate 60L (or anionic sample) is included, and the Aromatic 150 amount is increased to 1.08 g.

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation.

Spontaneity is recorded according to the following criteria: (1) poor: very thin emulsion cloud with major separation of oil droplets; (2) fair: thin emulsion cloud with minor separation of oil droplets; (3) good: thin emulsion cloud reaches the bottom of the cylinder without separation of any type; (4) excellent: thick emulsion cloud reaches the bottom of the cylinder without separation of any type.

Results are provided in Table 3. The ten samples indicated below are rated "good" overall as an anionic surfactant.

TABLE 3

Performance as an Anionic Emulsifier: % Separation

|  | 34 ppm water | | | 1000 ppm water | | |
| --- | --- | --- | --- | --- | --- | --- |
|  | Spont. | 1 h | 24 h | Spont. | 1 h | 24 h |
| Control 1 | G | <0.2 C | 1.3 C | G | <0.2 C | 1.3 C |
| Control 2 | F | 4 C | 4.4 C | F | 4 C | 4.4 C |
| C10-1 | F | 3.5 C | 4 C | F | 3.2 C | 4 C |
| C10-32 | F | 3 C | 3.9 C | F | 2.5 C | 3 C |
| C10-35 | F | 3 C | 3 C | F | 3.4 C | 4 C |
| C12-35 | F | 3.8 C | 5 C, Tr | F | 3 C | 4 C, Tr |
| C12-36 | F | 3.8 C | 4.5 C, Tr | F | 3.6 C | 4 C, Tr |
| C12-37 | F | 3 C | 4 C, <1 O | F | 3 C | 3 C, 1 O |
| C16-1 | F | 3.8 C | 4.1 C | F | 3 C | 3.8 C |
| C18-1 | F+ | 3.2 C | 3.9 C | F+ | 3.9 C | 4.1 C |
| C18-63 | F | 3.1 C | 3 C, 1 O | F | 3 C | 2.5 C, 1 O |
| C18-64 | F− | 3.2 C | 2.5 C, 1 O | F− | 3.7 C | 3 C, 1 O |

"C" denotes separation in the form of a cream, not a creamy oil or an oil. "Tr" denotes trace of oil observed.
"O" denotes oil separated
"Spon." = spontaneity or bloom, rated as E (excellent), G (good), F (fair), P (poor).
Control 1 = native anionic; control 2 = no anionic emulsifier.

Water-Soluble Herbicide Formulation Testing

Surfactant candidates for water soluble herbicide applications are examined as a replacement for the anionic, nonionic, or anionic/nonionic blend portion and compared to a known industry adjuvant standard for use in paraquat, a water soluble herbicide concentrate formulation. An emulsion solubility test is conducted whereby the concentrates are diluted in water to determine if solubility is complete. Results of the solubility testing appear in Table 4.

Control:

Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in mL) and type of separation are recorded after 30 min., 1 h, 2 h, and 24 h.

Anionic Test Sample:

Paraquat (4.57 g of 43.8% active material) is added to a 20-mL glass vial. An eight to ten mole alkyl phenol ethoxylate (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Nonionic Test Sample:

Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Adjuvant (Anionic/Nonionic) Test Sample:

Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Criteria for emulsion solubility: Test samples should be as good or better than the control with no separation after one hour. Two samples performs as well as or better than the control in the emulsion stability test.

TABLE 4

Water Soluble Herbicide Formulation:
Emulsion stability, mL separation

| test | Anionic | | | Nonionic | | | Adjuvant | | | |
| --- | --- | --- | --- | --- | --- | --- | --- | --- | --- | --- |
| sample | sol | 1 h | 24 h | sol | 1 h | 24 h | sol | 1 h | 24 h | Rating |
| C10-1 | S | 0 | 0 | D | 1 | 1 | S | 0 | 0 | good |
| C10-32 | S | 0 | 0 | D | 1 | 1 | D | 0 | Tr | good |

D = dispersable; S = soluble
Control result: Solubility: D; 1 h: 0 mL; 24 h: Tr.

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic. Here, the samples are anionic (sulfonates).

Anionic Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, product of Stepan), test sample (0.29 g if 100% active material), and deionized water (to 100.0 g solution). The control sample for anionic testing replaces the test sample with Stepanol® WA-Extra PCK (sodium lauryl sulfate, Stepan, 1.0 g, nominally 30% active material).

Soil Composition:

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica 1 (8), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J. M. Smucker (1), olive oil (3), linoleic acid (3), and squalene (3).

Four sulfonates and eleven sulfo-estolides perform as well as or better than the control in this test (see Tables 5 and 6).

TABLE 5

Control Runs for Gardner Straight Line Washability Test

| | Ave. % clean after 2, 4, 6, 8, or 10 swipes | | | | |
|---|---|---|---|---|---|
| | 2 | 4 | 6 | 8 | 10 |
| Control 1 | 52.4 | 59.0 | 62.5 | 62.8 | 63.9 |
| Control 3 | 54.6 | 61.4 | 64.3 | 68.4 | 72.2 |
| Control 5 | 50.8 | 59.2 | 63.9 | 65.3 | 67.1 |
| Control 8 | 49.6 | 55.9 | 56.8 | 62.8 | 64.1 |
| Control 9 | 55.5 | 61.5 | 66.0 | 65.9 | 68.4 |
| Control 10 | 60.3 | 63.5 | 66.2 | 65.8 | 68.7 |
| Control 15 | 59.7 | 63.6 | 64.5 | 69.5 | 69.5 |
| Control 16 | 50.9 | 61.5 | 63.1 | 64.0 | 67.7 |
| Control 17 | 54.7 | 63.7 | 64.6 | 66.1 | 69.6 |
| Control 20 | 65.0 | 70.7 | 72.2 | 73.7 | 74.0 |
| Control 24 | 52.8 | 61.6 | 63.3 | 64.9 | 65.7 |

TABLE 6

Gardner Straight-Line Washability Anionic Test Samples

| | | | Ave. % clean | | | | | |
|---|---|---|---|---|---|---|---|---|
| Sample | Control # | Compound class | 2 | 4 | 6 | 8 | 10 | Rating |
| C10-1 | 10 | sulfonate | 61.8 | 65.6 | 68.0 | 68.7 | 70.5 | equal |
| C10-33 | 1 | sulfo-estolide | 52.6 | 58.8 | 67.6 | 69.2 | 69.9 | superior |
| C10-34 | 3 | sulfo-estolide | 52.2 | 59.4 | 61.3 | 63.8 | 65.3 | equal |
| C10-35 | 5 | sulfo-estolide | 57.1 | 64.8 | 68.2 | 70.5 | 72.5 | equal |
| C12-1 | 16 | sulfonate | 52.6 | 60.9 | 62.6 | 65.5 | 68.0 | equal |
| C12-34 | 8 | sulfo-estolide | 52.2 | 59.4 | 61.3 | 63.8 | 65.3 | equal |
| C12-35 | 9 | sulfo-estolide | 57.1 | 64.8 | 68.2 | 70.5 | 72.5 | equal |
| C12-36 | 9 | sulfo-estolide | 58.2 | 62.0 | 68.0 | 70.9 | 72.5 | equal |
| C12-37 | 9 | sulfo-estolide | 56.3 | 65.8 | 68.3 | 71.1 | 72.3 | equal |
| C12-43 | 24 | sulfo-estolide | 57.8 | 62.6 | 64.3 | 64.9 | 66.2 | equal |
| C12-44 | 24 | sulfo-estolide | 58.6 | 62.9 | 64.4 | 65.6 | 67.0 | equal |
| C16-1 | 20 | sulfonate | 62.7 | 69.2 | 69.4 | 70.2 | 70.2 | equal |
| C18-1 | 15 | sulfonate | 52.7 | 59.2 | 59.6 | 62.1 | 64.0 | equal |
| C18-63 | 17 | sulfo-estolide | 52.4 | 55.3 | 64.2 | 66.0 | 66.9 | equal |
| C18-64 | 17 | sulfo-estolide | 52.2 | 62.0 | 64.6 | 65.6 | 67.0 | equal |

Hard-Surface Cleaners: Foaming Glass and Window Cleaner

Control: Ammonyx® LO (lauramine oxide, 0.70 g, product of Stepan) and Bio-Terge® PAS-8S (2.00 g, sodium caprylyl sulfonate, product of Stepan) are combined with isopropyl alcohol (2.50 g) and diluted to 100 mL with deionized water.

Test formulation: Test sample (0.21 g) and Bio-Terge PAS-8S (2.00 g) are combined with isopropyl alcohol (2.50 g) and diluted to 100 mL with deionized water.

Method: The test formulation is evaluated for clarity; only clear formulations are evaluated in the low film/low streak test. The test measures the ability of the cleaner to leave a streak and film-free surface on a test mirror. The test formula is applied to a mirror in a controlled quantity and wiped with a standard substrate back and forth, leaving the spread product to dry. Once dry, the mirrors are inspected and evaluated by a two-person panel. Ratings of "better than," "equal" or "worse than" the control are assigned. The formulation used here is used to evaluate amphoteric and nonionic surfactants.

One test sample, C12-1, performs equal to the control.

Oil Field Products: Paraffin Dispersants

Asphaltenes Sceening Test

During acid stimulation of an oil well, a blend of HCl, HF, and corrosion inhibitor is pumped down a well, allowed to stand, and then pumped out. During the transfer of the acid, small amounts of iron chloride are developed in the acid solution. Once the acid blend dissolves scales and deposits in the well bore, crude oil begins to flow and mixes with the acid solution in the well. The crude oil can solidify after acidizing, and asphaltenes have been associated with the problem. Thus, dispersants are commonly added to the acid to prevent the solidification.

Test Method:

A stock solution of iron-contaminated acid is made by adding 1% $FeCl_3$ to a 15% HCl acid solution. The sample dispersant to be tested (0.2 wt. %) is added to the acid stock solution (7.5 mL). A 15-mL vial is charged with the acid/dispersant mixture and crude oil (2.5 mL), and the vial is shaken vigorously for 30 s. The initial appearance is recorded. After standing at room temperature for 1 h, the appearance is again noted. The vial is placed in an oven (50° C.) for 24 h and its appearance is recorded. The vial is allowed to cool to room temperature and appearance is again noted. Finally, after 24 h at room temperature, appearance is again noted. A blank sample containing crude oil and acid solution but no dispersant is run. A control sample containing soy amidoamine trimethylammonium chloride as the dispersant is also run. Yet another sample is run containing a 1:1 mixture of test dispersant and soy amidoamine trimethylammonium chloride.

One sample, C10-1, provides performance equal to the control in this test.

Performance in a Latex Paint Application

Emulsion Polymerization Surfactant Screen:

A reaction kettle is charged with sodium bicarbonate (0.50 g), water (225 g), and seed latex (30 g) and the mixture is heated to 83° C. under nitrogen with stirring at 200 rpm. In a 1-L beaker, surfactant C12-37 (10.0 g, 49.8% actives, 1.0% active surfactant in the latex) and water (150 g) are combined and stirred. Methyl methacrylate (255 g), butyl acrylate (235 g), and methacrylic acid (10 g) are combined in an Erlenmeyer flask and mixed. The monomer mixture is added to the beaker containing water and C12-37 with increasing agitator speed, and the resulting mixture is stirred 10 min. or until completely emulsified to give a monomer emulsion. Separately, two other mixtures are prepared: an initiator shot mixture of ammonium persulfate (1.0 g) in water (20 g), and a cofeed mixture of ammonium persulfate (2.70 g), sodium bicarbonate (1.50 g), and water (75 g); the total amount of initiator used is 0.74% based on monomers. The initiator shot is charged to the reaction kettle dropwise over 1 min, then held for 10 min. The monomer emulsion is then fed to the kettle at 2.1 mL/min. for 10 min. The feed rate of the monomer emulsion is increased to 4.2 mL/min., and the cofeed mixture is started at 0.37 mL/min. Total addition time is 3 h, during which particle size and temperature are monitored. After addition of the monomer emulsion is complete, a water wash (50 g) is started, and heating continues for 1 h. The product is cooled. The pH is adjusted to 7.5 with dilute ammonium hydroxide solution. A preservative is added, and the mixture is filtered. Final latex properties: 49% solids; coagulum/grit: 0.04% based on monomers. The latex is used to formulate a latex paint as described below and is compared with a control latex that contains a standard industry surfactant.

Latex Paint Formulation:

Titanium dioxide slurry (Dupont Ti-Pure® R746) is charged to a container, followed by deionized water and propylene glycol, and the contents are mixed (500 rpm). Latex (49% solids with C12-37), wetting agent (octylphenol ethoxylate), and preservative (Acticide® GA, product of Thor) are added. Thickener (Acrysol™ SCT-275, product of Dow) is slowly charged below the liquid surface by syringe. The pH is adjusted to 9.0 using ammonium hydroxide solution. The batch is mixed for 30 min. and then allowed to stand for at least 2 h. The batch is remixed gently, and a portion (220 g) is transferred to a 400-mL beaker. Solvent ($C_{18}$ amide, 0.5% VOC, EPA Method 24, 5 wt. % based on latex solids) is added and mixed at 650 rpm. Viscosity is adjusted to an initial KU of 90 with more thickener. The paint is covered and final KU is measured after 24 h. Its value falls within the range of 93-100 KU and varies from the original measurement by no more than 5 KU.

Example formulation: $TiO_2$ (solids basis): 22.71 wt. %; water: 52.73 wt. %; propylene glycol 2.27 wt. %; latex with 012-37 (solids basis; 1% active derivative) 20.14%; ammonium hydroxide: 0.31 wt. %; preservative: 0.09 wt. %; control additive (solvent): 1.15 wt. %; wetting agent; 0.17 wt %; thickener: 0.43 wt. %. PVC: 22.1%. VOC: <50 g/L. Final KU: 98.6.

Wet Scrub Resistance/ASTM 2486 Modified:

Wet scrub resistance based on a modified version of ASTM-2486-00, method B; modified to % weight loss, is performed for each paint formulation. Paints are applied to Leneta P-121-10N plastic panels using a 13-cm wide, 10-mil wet film applicator and dried under ambient conditions for five days prior to testing. The coated panels are then cut into strips (16.5 cm×5.7 cm, two per drawdown). The strips are weighed prior to testing. Two samples at a time are placed on a Gardner Company scrub tester with approximately a 2" gap between the samples and taped to secure panels to the machine. A spacer is placed over the samples to maintain the scrub brush pathway and further secure the samples. A scrub brush (8 cm×3 cm), preconditioned in room temperature water, is inserted into the holder. Scrub compound (10 g, supplied by Leneta Company as "ASTM-2486 scrub compound") is applied evenly to the brush. Water (5 g) is placed into the gap between the samples. Samples are tested to 1200 cycles. Additional scrub compound (10 g) and water (5 g) are reapplied every 300 cycles. The strips are then rinsed under tepid water and dried for 24 h. The strips are reweighed and the % coating removed is determined.

Gloss Determination—60°/20°—ASTM D523

Paints are applied to Leneta P-121-10N plastic panels using a wet film applicator (13 cm×10 mil) and dried under ambient conditions for 5 days prior to testing. Gloss is measured with an ASTM accepted glossmeter (Gardco).

Results:

One sulfonate sample, C12-37, performs as well as the control surfactants (see Table 7).

TABLE 7

| Performance in a Latex Paint Application | | | |
|---|---|---|---|
| | 60° gloss | 20° gloss | % coating removed, scrub |
| Control 1 | 64 | 17.6 | 2.42 |
| Control 2 | 73.7 | 29.6 | 2.38 |
| C12-37 | 76.9 | 36.0 | 2.36 |

The preceding examples are meant only as illustrations. The following claims define the invention.

We claim:

1. A composition comprising a mixture of:

a β-hydroxy-substituted alkanesulfonate and an alkenesulfonate;

wherein the composition has the structure:

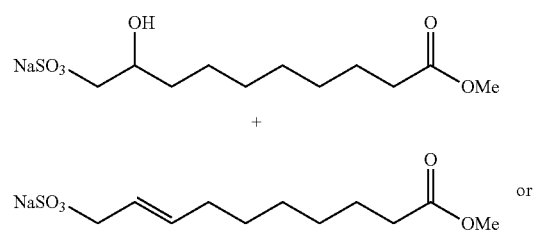

-continued
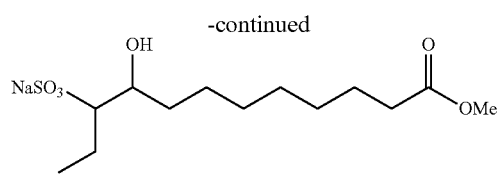
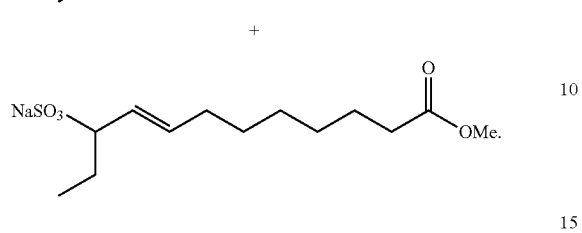
2. A sulfo-estolide having a structure selected from the group consisting of:
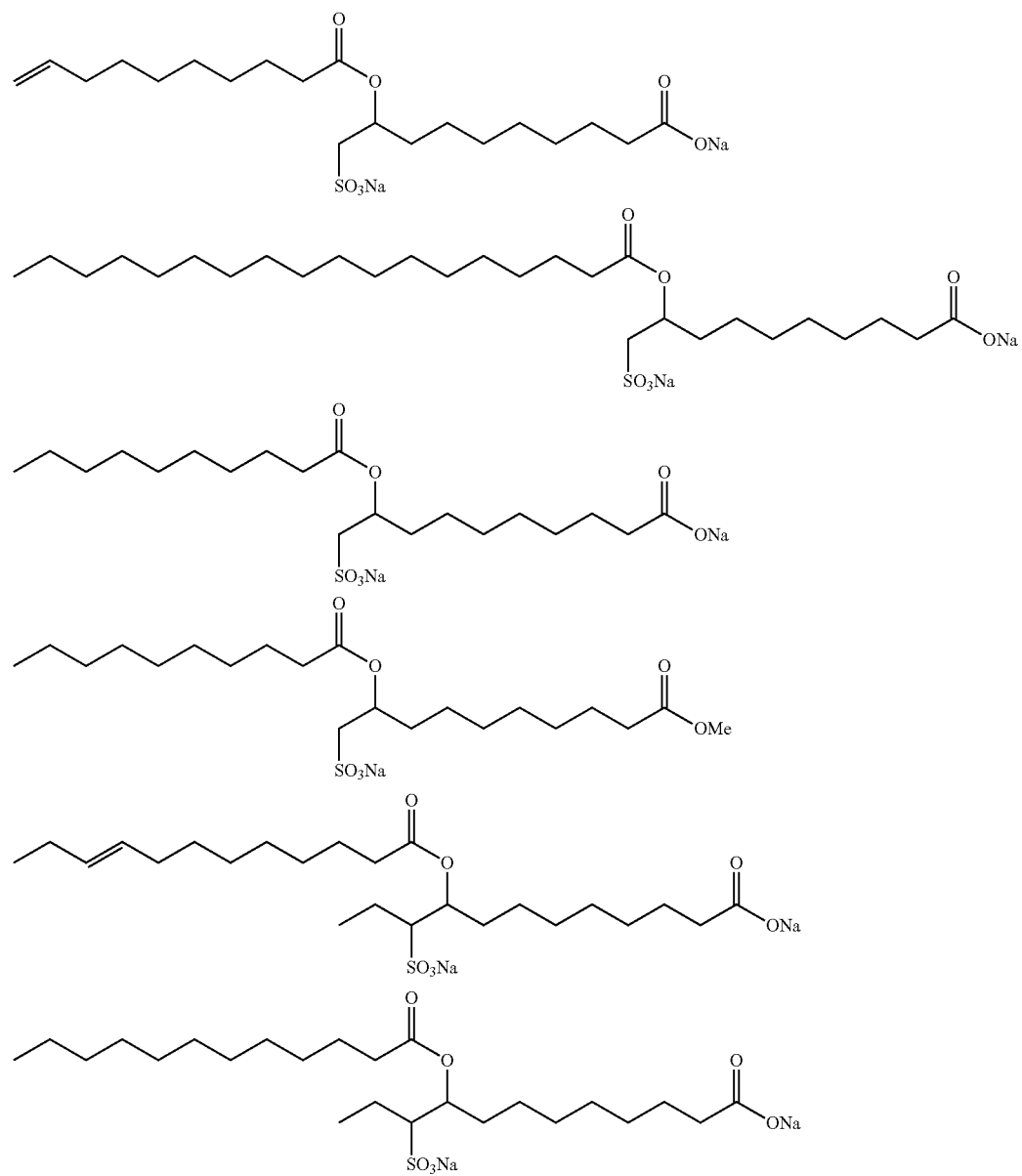

-continued

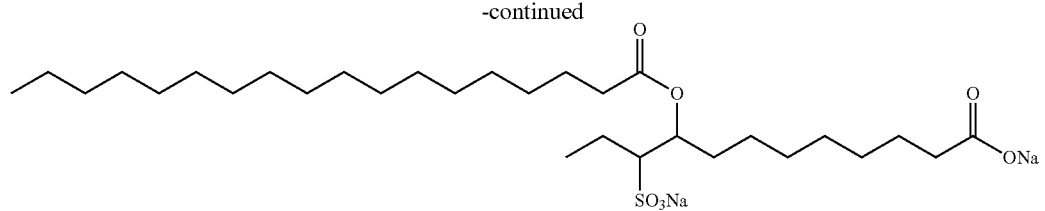

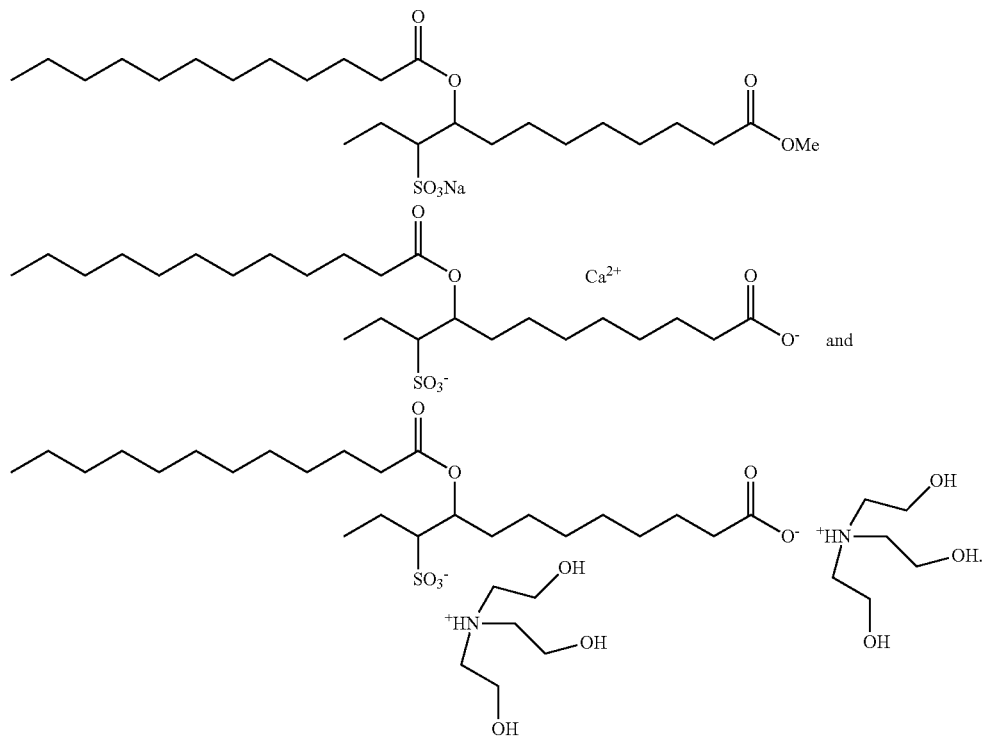

3. An anionic emulsifier for agricultural compositions, a water-soluble herbicide composition, an aqueous hard-surface cleaner, a paraffin dispersant for oilfield applications, or a paint or coating additive composition comprising the composition of claim 1.

4. An anionic emulsifier for agricultural compositions, a water-soluble herbicide composition, an aqueous hard-surface cleaner, a paraffin dispersant for oilfield applications, or a paint or coating additive composition comprising the composition of claim 2.

5. A sulfonate composition having the structure:

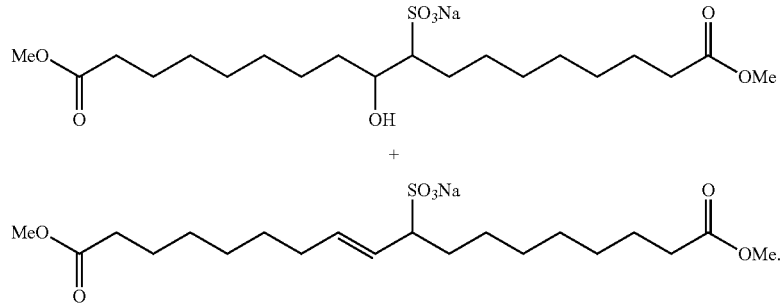

6. An anionic emulsifier for agricultural compositions, a water-soluble herbicide composition, an aqueous hard-surface cleaner, a paraffin dispersant for oilfield applications, or a paint or coating additive composition comprising the sulfonate composition of claim 5.

7. A sulfo-estolide having the structure:

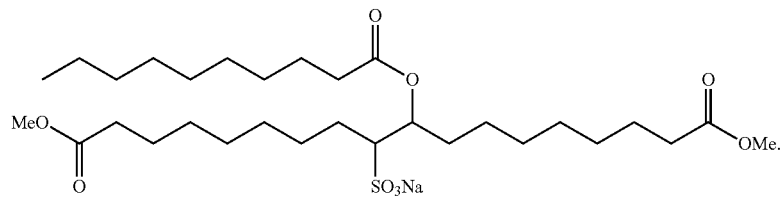

8. An anionic emulsifier for agricultural compositions, a water-soluble herbicide composition, an aqueous hard-surface cleaner, a paraffin dispersant for oilfield applications, or a paint or coating additive composition comprising the sulfo-estolide of claim 7.

* * * * *